United States Patent [19]

Battisti et al.

[11] 4,149,005

[45] Apr. 10, 1979

[54] PROCESS FOR PREPARING 1-PHENYL-3-AMINOPYRAZOLES

[75] Inventors: Ruggero Battisti; Luigi Cassar; Nicola Mazzaferro, all of Novara, Italy

[73] Assignee: Montedison S.p.A., Milan, Italy

[21] Appl. No.: 809,849

[22] Filed: Jun. 24, 1977

[30] Foreign Application Priority Data

Jun. 25, 1976 [IT] Italy .............................. 24718 A/76

[51] Int. Cl.$^2$ .......................................... C07D 231/38
[52] U.S. Cl. .................................. 548/362; 260/162
[58] Field of Search ......................................... 548/362

[56] References Cited

FOREIGN PATENT DOCUMENTS 226388 1/1960 Australia ................................. 548/362
371227 4/1973 U.S.S.R. ................................. 548/379

OTHER PUBLICATIONS

Elderfield, *Heterocyclic Compounds*, vol. 5, pp. 108–109, N.Y., Wiley, 1957.

Fusco, *Pyrazoles*, in: *Pyrazoles, Pyrazolines, Pyrazolidenes, Indazoles and Condensed Rings*, pp. 41–45, N.Y. Interscience, 1967.

*Primary Examiner*—Natalie Trousof
*Assistant Examiner*—Natalia Harkaway

[57] ABSTRACT

1-phenyl-3-amino-2-pyrazolines are catalytically oxidized to 1-phenyl-3-aminopyrazoles, using oxygen and/or air as the oxidizing agent and in the presence of copper salts, optionally associated with metallic copper and/or an aromatic, heterocyclic organic base selected from N-dialkyl anilines, pyridines, piperidine, and ethanolamine, or equivalents thereof, in an inert reaction medium and at a temperature of from about 20° C. to about 40° C.

5 Claims, No Drawings

PROCESS FOR PREPARING 1-PHENYL-3-AMINOPYRAZOLES

THE PRIOR ART

The preparation of 1-phenyl-3-amino-2-pyrazolines by condensation of phenylhydrazines with acrylonitrile in a sodium ethylate solution, is known in the art. The oxidation of 1-phenyl-3-amino-2-pyrazolines to the corresponding 1-phenyl-3-aminopyrazoles is also known. Such oxidation can be accomplished according to the art, by different methods.

One method consists in protecting the amino-group of the pyrazoline by condensation with organic acids or aldehydes, thereafter oxidizing, with $KMnO_4$, the amides or, respectively, azomethines obtained and, finally, saponifying.

According to another method, the pyrazoles of the present invention can be prepared starting from the acetylderivative of the corresponding pyrazoline by treatment thereof with sulphur at high temperatures, followed by acid saponification.

The foregoing are technologically complicated, multistage methods, in which oxidation is conducted stoichiometrically, and which give, in any case, yields which are low for industrial uses.

According to a further method, 1-phenyl-3-amino-2-pyrazoline is oxidized by using chloranil (tetrachloro-p-benzoquinone) or by employing ferric sulphate in sulphuric acid, according to substantially stoichiometric reactions. The yields, however, are not satisfactory, and these last-mentioned processes have few possibilities of being used industrially.

THE PRESENT INVENTION

One object of the present invention is to provide a simple and economical method for preparing 1-phenyl-3-aminopyrazoles free from the drawbacks of the prior art methods.

This and other objects, that will appear more clearly to those skilled in the art from the following description, are achieved by a process for preparing 1-phenyl-3-aminopyrazoles having the general formula (I):

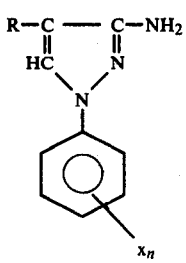
(I)

where: R is H or $CH_3$; X is H, Br, Cl, alkyl, alkoxyl or carboxyalkyl groups with from 1 to 4 carbon atoms or $CF_3$; and n is 1 or 2, through oxidation of 1-phenyl-3-amino-2-pyrazolines having the general formula (II):

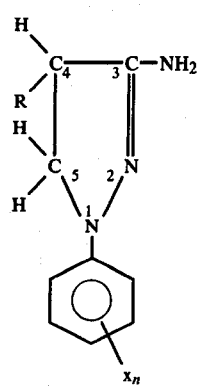
(II)

in which R, X and n have the same meaning as indicated hereinabove; characterized in that the oxidation is conducted with oxygen and/or air in the presence of copper salts, optionally associated with metallic copper and/or an organic base selected from the group consisting of N-dialkylanilines, pyridines, piperidine, ethanolamine, or equivalents thereof, in an inert reaction medium, and at a temperature comprised between about 20° and 40° C.

The oxidizing agent is oxygen or air, mixtures of oxygen with inert gases, such as nitrogen, being also useful.

The catalysts are inorganic or organic cuprous and/or cupric salts, such as CuCl, $CuCl_2$, sulphates, acetates, etc., optionally associated with suitable amounts of metallic copper and/or of the organic bases mentioned hereinabove, or equivalents thereof.

The reaction is conducted in a solvent which is inert under the reaction conditions.

Suitable solvents are the low molecular weight alcohols, for instance from methyl to butyl alcohol, acetonitrile, acetic acid, chlorobenzenes, etc. The solvent may be used with minor amounts of water, for example of the order of 10–15% of the total solvent up to about 50%.

The reaction rate can be improved by adding small amounts of an organic base as described hereinabove to the catalytic system; amounts of up to about 10% by moles in respect of the pyrazoline (II) moles are sufficient.

The reaction is conducted at a temperature ranging from about 20° to 40° C. and is slightly exothermic.

The concentration of the reagents in the reaction medium may vary over a wide range. One can operate in a suspension, while an intense stirring, brought about, for example, by shaking or by a screw device, promotes intimate contact of the reagents.

The amount of catalyst used is not critical and may vary in a wide range. Good results have been obtained by using amounts ranging from 5 to 7% by weight expressed as moles of metal Cu in respect of the introduced moles of 1-phenyl-3-amino-2-pyrazoline. Larger amounts are not harmful and may be used.

The copper salts can be used in association with metallic copper, also in an amount of 50% of the copper present, especially with the cupric salts. This leads to an improvement of the reaction rates and also facilitates filtration of the reaction mass for recovering and recycling the catalyst.

Reaction times of from 2 to 4 hours are sufficient to complete the reaction. The separation of the resulting 1-phenyl-3-amino-pyrazole from the reaction mass is carried out according to substantially conventional methods: for example, after removal of the solvent by distillation, through extraction with suitable hydrocarbon solvents such as n-heptane, ethers or with hydrochloric acid, and through successive neutralization with NaOH, etc.

According to one effective embodiment of this invention, the process is conducted as follows:

1-phenyl-3-amino-2-pyrazoline, copper salt (CuCl) and metallic copper, if any, and/or pyridine, in the form of a suspension or of a solution in the solvent (e.g., ethyl alcohol) are introduced, in the desired amounts (between 5 and 6%), into a reactor equipped with feeding systems for reagents and with an effective stirrer. Stirring is started in an oxygen atmosphere. After about 2 hours, oxidation is concluded and the whole solid is dissolved. The catalyst is filtered, the solvent is distilled under vacuum, and the 1-phenyl-3-aminopyrazole is isolated by extraction with, e.g., n-heptane. Additional 1-phenyl-3-aminopyrazole is recovered by treating the n-heptane extraction residue with diluted hydrochloric acid, followed by neutralization with aqueous NaOH to precipitate the 1-phenyl-3-aminopyrazole. Optionally, the heptane extraction residue diluted with hydrochloric acid can be clarified with animal charcoal, prior to neutralization thereof. As is known, the 1-phenyl-3-aminopyrazoles are an important class of products which are valuable for various industrial uses, such as active intermediates in the preparation of dyestuffs, of sensitive agents for use in photography, and of other fine chemicals.

The present process for preparing the 1-phenyl-3-aminopyrazoles has the advantages of making production thereof possible under mild operating conditions and of giving high yields of very pure products.

The following examples are given to illustrate the process of the invention in more detail and are not intended to be limiting. Example 15 describes the preparation of a dye obtained from 1-phenyl-3-aminopyrazole prepared according to this invention, and Example 16 shows the application of said dye to a polyester fabric.

EXAMPLE 1

In a flask, 5 g (0.031 mole) of 1-phenyl-3-amino-2-pyrazoline were suspended in 25 ml of ethanol with addition of 0.2 g (0.00201 mole) of CuCl, and the flask was put, under an oxygen head, into a shaking apparatus at room temperature. Oxidation was completed after about 2 hours: the chromatographic analysis on a thin layer revealed that there was no longer any starting product, the whole solid having dissolved.

The catalyst was filtered and, after removal of the solvent under vacuum, 1-phenyl-3-aminopyrazole (I) was isolated by extraction with n-heptane, from which 3.5 g were crystallized as white needles melting at 89°–90° C. The extraction residue was treated with dilute HCl and from the latter, after clarification with animal charcoal and through neutralization with aqueous NaOH, a further 0.3 g of 1-phenyl-3-aminopyrazole (I), of m.p. 88°–89° C., was obtained. 3.8 g of product (I) were obtained in the aggregate, the yield being about 76% of the theoretical value.

EXAMPLE 2

Using the same apparatus as in Example 1 and following the same modalities, 5 g (0.031 mole) of 1-phenyl-3-amino-2-pyrazoline were suspended in 25 ml of ethanol with the addition of 0.1 g (0.001 mole) of CuCl and of 0.064 g (0.001 mole) of metallic Cu, under an oxygen head, at a temperature of 30° C. After about 2 hours, the oxidation was completed and the whole solid was dissolved. The catalyst was filtered and, after removal of the solvent under vacuum, 1-phenyl-3-aminopyrazole (I) was hot extracted with diluted HCl from which, after clarification with animal charcoal, 4 g of product (I) precipitated in the form of whitish needles by neutralization with aqueous NaOH. The melting point of the product was 89°–90° C.; the yield was about 80% of the theoretical value.

EXAMPLE 3

Example 1 was repeated using the following amounts of reagents: 5 g (0.031 mole) of 1-phenyl-3-amino-2-pyrazoline were suspended in 25 ml of ethanol and 2 ml of $H_2O$, under addition of 0.1 g (0.001 mole) of CuCl and 0.064 g (0.001 mole) of Cu, under an oxygen head. Oxidation lasted about 3 hours. 3.9 g of 1-phenyl-3-aminopyrazole were obtained.

EXAMPLE 4

Example 1 was repeated using the following amounts of reagents: 5 g (0.031 mole) of 1-phenyl-3-amino-2-pyrazoline were dissolved in 25 ml of acetonitrile under addition of 0.2 g (0.00201 mole) of CuCl, under an oxygen head. Oxidation lasted about 3 hours. 2.5 g of 1-phenyl-3-aminopyrazole were obtained.

EXAMPLE 5

Using the same apparatus as in Example 1 and following the same modalites, 5 g (0.031 mole) of 1-phenyl-3-amino-2-pyrazoline were dissolved in 15 ml of acetic acid with addition of 0.2 g (0.00201 mole) of CuCl, under an oxygen head. Oxidation was completed after about 5 hours. Acetic acid was neutralized with sodium bicarbonate, it was filtered and the precipitate was extracted with ether. By evaporating the ethereal solution, 1.5 g of 1-phenyl-3-aminopyrazole were obtained.

EXAMPLE 6

In a breaker equipped with a turbine stirrer, 2.5 g (0.0155 mole) of 1-phenyl-3-amino-2-pyrazoline were suspended in 50 ml of methanol with addition of 0.1 g (0.001 mole) of CuCl, under an air head. After about 2 hours no starting product was noticed any longer. The oxidation product was recovered as in Example 1, 1.5 g of 1-phenyl-3-aminopyrazole being obtained.

EXAMPLE 7

Example 2 was repeated, with the only exception that the catalyst was composed of 0.1 g (0.000586 mole) of $CuCl_2.2H_2O$ and by 0.064 g (0.001 mole) of Cu, under an oxygen head. Oxidation was completed after about 3 hours. 3.8 g of 1-phenyl-3-aminopyrazole having a melting point of 89°–90° were obtained.

EXAMPLE 8

In the same apparatus as in Example 1 and according to the same modalities, 2.5 g (0.0143 mole) of 1-phenyl-3-amino-4-methyl-2-pyrazoline were suspended in 20 ml of methanol with addition of 0.1 g of CuCl, under an air head. After about 12 hours, the starting product was no longer noticed. The oxidized product was recovered as in Example 1, 1.5 g of 1-phenyl-3-amino-4-methyl-pyrazole having a melting point of 121°–122° C. being obtained.

EXAMPLE 9

In the same apparatus and following the same modalities as in Example 1, 1 g (0.00416 mole) of 1-(p-bromophenyl)-3-amino-2-pyrazoline was suspended in 10 ml of ethanol with addition of 0.04 g (0.0004 mole) of CuCl and of 0.013 g (0.0002 mole) of Cu, under an oxygen head. Oxidation was concluded after about 3 hours. The oxidized product was recovered as in Example 1, thus obtaining 0.5 g of 1-(p-bromophenyl)-3-aminopyrazole, of melting point 122°–123° C.

EXAMPLE 10

In the same apparatus and following the same modalities as in Example 1, 5 g (0.0255 mole) of 1-(m-chlorophenyl)-3-amino-2-pyrazoline were suspended in 25 ml of ethanol with addition of 0.2 g of CuCl, under an oxygen head. Oxidation was concluded after about 3 hours. The oxidized product was recovered as in Example 1, obtaining 3.6 g of 1-(m-chlorophenyl)-3-aminopyrazole, melting at 106°–107° C.

EXAMPLE 11

In the same apparatus and according to the same modalities as in Example 1, 1.95 g (0.01 mole) of 1-(p-chlorophenyl)-3-amino-2-pyrazoline were suspended in 12 ml of ethanol and 0.1 ml of pyridine with addition of 0.1 g of CuCl, under an oxygen head. Oxidation was completed after about 10 hours. The oxidized product was isolated as in Example 2, thus obtaining 1 g of 1-(p-chlorophenyl)-3-amino-pyrazole of melting point 107°–108° C.

EXAMPLE 12

In a beaker provided with a turbine stirrer and thermometer, were suspended 22.9 g (0.1 mole) of 1-(m-trifluoromethylphenyl)-3-amino-2-pyrazoline, 0.78 g (0.0079 mole) of CuCl, 0.15 ml of piperidine in 97 ml of o-dichlorobenzene and air was bubbled through the mixture, by means of a drawing pipe, under stirring.

After about 2 hours, oxidation was completed. To the filtered chlorobenzene solution there were then added 20 ml of concentrated HCl and 100 ml of water and the solvent was removed by distillation in a steam current. Thereupon, the residual acid solution was filtered, and after mixing with citric acid for complexing possibly dissolved copper, was neutralized with an aqueous solution of NaOH to precipitate 17 g of 1-m(trifluoromethylphenyl)-3-aminopyrazole which had a melting point of 80° C. and the following elementary analysis:

For $C_{10}H_8F_3N_3$—Theoretical: C=52.86%, H=3.52%; N=18.50%. Found: C=52.78%; H=3.50%; N=18.50%.

EXAMPLE 13

Operating according to the procedures and same molar amounts indicated in Example 12, on 23 g (0.1 mole) of 1-(3,4-dichlorophenyl)-3-amino-2-pyrazoline, there were obtained 11.04 g of 1-(3,4-dichlorophenyl)-3-aminopyrazole which had a melting point ranging from 120° to 121° C. and gave the following percentual analysis:

For $C_9H_7Cl_2N_3$—Theoretical: C=47.37%; H=3.07%; Cl=31.14%; N=18.42%. Found: C=47.24%; H=3.02%; Cl=30.85%; N=18.27%.

EXAMPLE 14

In a flask were suspended: 2.33 g (0.01 mole) of 1-(m-carboxyethyl-phenyl)-3-amino-2-pyrazoline; 0.078 g (0.00079 mole) of CuCl and 0.05 g of piperidine in 15 ml of o-dichlorobenzene and, under an oxygen head, the flask was placed on a rocker, the mixture being subjected to stirring at room temperature. Oxidation was completed in about 2 hours. Thereupon, the chlorobenzene solution was extracted with diluted hydrochloric acid and from the acid solution, after clarification with animal charcoal and admixture of citric acid, by neutralization with aqueous NaOH there were obtained 1.86 g of 1-(m-carboxyethyl-phenyl)-3-aminopyrazole that had a melting point of 92°–93° C. and gave the following percentual analysis:

For $C_{12}H_{13}N_3O_2$—Theoretical: C=62.34%; H=5.63%, N=18.18%. Found: C=62.50%, H=5.76%; N=18.23%.

EXAMPLE 15

Preparation of a Dye 1.59 g (0.01 mole) of 1-phenyl-3-aminopyrazole were dissolved in 60 ml of $H_2O$ containing 5 ml of concentrated HCl and were diazotized at 0.5° C. with 0.75 g of $NaNO_2$ dissolved in 5 ml of $H_2O$. Nitrite in excess was eliminated with sulphamic acid.

The solution of the resulting diazo-derivative was dropped into a solution consisting of 1.74 g (0.01 mole) of 1-phenyl-3-methyl-5-pyrazolone, of 5 ml of 30% NaOH and of 50 ml of $H_2O$, kept at 0°–50° C. At the conclusion of the coupling, the mass was acidified with HCl, filtered, and washed with water, thus obtaining, after drying, 3.1 g of a yellow powder having the structure:

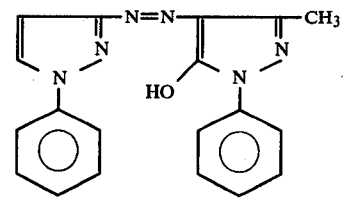

which was confirmed by the centesimal analysis and the molecular weight.

EXAMPLE 16

Dyeing

In a dyeing apparatus under pressure, 100 g of a polyester fabric, previously scoured, were treated for 10–15 minutes in a 2 liter dyeing bath at 50° C. containing 2 g/l of ammonium sulphate and 1 g/l of Emulsion ELU (a non-ionogenic surfactant, produced by Montedison). 1 g of a dye prepared according to Example 15, previously dispersed and filtered through a screen, was added thereto.

The bath was brought to a pH of 5.5 with formic acid, heated to 90° C. in 20–30 minutes, after which the temperature was gradually raised until reaching 130° C., at which temperature the bath was kept for 60 minutes. At the conclusion of the dyeing, it was cooled down to 80°–85° C., the bath was discharged, the fabric was rinsed and a reducing alkaline treatment was carried on for 20 minutes at 80° C. by means of a bath containing 2 ml/l of caustic soda at 36 Be, 2 g/l of Albite A ($Na_2S$-

$_2O_4$ at 85%) and 0.5 g/l of Diapal CW (a non-ionogenic detergent produced by Montedison). The dyed fabric was repeatedly rinsed and dried. It was dyed to a yellow shade of good intensity and stability to sunlight and to wet conditions.

What we claim is:

1. Process for preparing a phenyl-3-aminopyrazole having the formula:

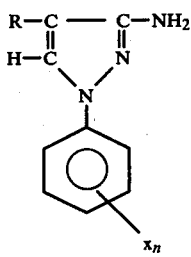
(I)

in which

R is H or $CH_3$;

X is H, Br, Cl, $CF_3$ or an alkyl, alkoxyl or carboxyl alkyl group having from 1 to 4 carbon atoms and n is 1 or 2, which process consists in oxidizing a 1-phenyl-3-amino-2-pyrazoline of the formula:

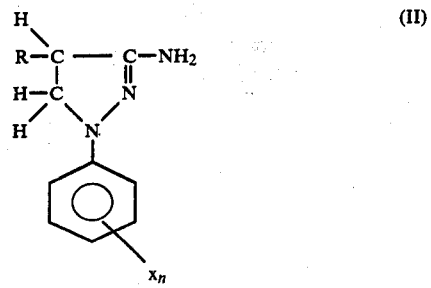
(II)

in which R, X and n have the same meaning as in formula (I), in an atmosphere of oxygen and/or air, in the presence of at least a copper salt as catalyst and in a total amount of at least 5% by weight expressed as moles of metal Cu in respect of the moles of 1-phenyl-3-amino-2-pyrazoline introduced, in an inert reaction medium, and at a temperature of from about 20° C. to about 40° C.

2. The process of claim 1, in which the oxidation is conducted in the presence of at least a copper salt selected from the group consisting of CuCl, $CuCl_2$, $CuSO_4$, and cupric or cuprous acetate.

3. The process of claim 1, in which the copper salt is employed in association with metallic copper and/or with an organic base selected from the group consisting of N,N-dialkylaniline pyrine, piperidine and ethanolamine.

4. The process of claim 1, in which the oxidation is conducted in a medium selected from the group consisting of lower alcohols, acetonitrile, acetic acid, chlorobenzene, also in the presence of lesser amounts of $H_2O$.

5. The process of claim 4, in which the medium in which the oxidation is conducted contains a minor amount of water.

* * * * *